United States Patent
Arnold, Jr. et al.

(10) Patent No.: US 6,387,117 B1
(45) Date of Patent: May 14, 2002

(54) STENT CRIMPING SYSTEM

(75) Inventors: John E. Arnold, Jr., Minneapolis; Terry V. Brown, Fridley; Andrew J. Dusbabek, Dayton, all of MN (US); Christopher J. Elliott, Hopkinton, MA (US); Louis G. Ellis, St. Anthony; Christopher R. Larson, St. Paul, both of MN (US); Gary J. Leanna, Rutland, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/401,213

(22) Filed: Sep. 22, 1999

(51) Int. Cl.[7] ................................................ A61B 17/00
(52) U.S. Cl. ............................. 623/1.1; 606/207; 72/416
(58) Field of Search ............................... 606/1, 108, 198, 606/207, 205, 210, 211; 623/1.1, 12; 81/424.5; 72/409.08, 409.13, 409.19, 416; 294/99.1, 99.2, 106, 118

(56) References Cited

U.S. PATENT DOCUMENTS

| | | | |
|---|---|---|---|
| 2,948,171 A | * | 8/1960 | Lucibello ..................... 81/418 |
| 5,026,377 A | | 6/1991 | Burton et al. |
| 5,138,864 A | * | 8/1992 | Tarpill ......................... 72/416 |
| 5,183,085 A | | 2/1993 | Timmermans |
| 5,290,305 A | | 3/1994 | Inoue |
| 5,381,686 A | | 1/1995 | Thorup |
| 5,411,521 A | | 5/1995 | Putnam et al. |
| 5,437,083 A | | 8/1995 | Williams et al. |
| 5,509,184 A | | 4/1996 | Herrero |
| 5,546,646 A | | 8/1996 | Williams et al. |
| 5,591,222 A | | 1/1997 | Susawa et al. |
| 5,626,604 A | | 5/1997 | Cottone, Jr. |
| 5,628,754 A | | 5/1997 | Shevlin et al. |
| 5,630,830 A | | 5/1997 | Verbeek |
| 5,672,169 A | | 9/1997 | Verbeck |
| 5,692,294 A | * | 12/1997 | Casey ......................... 72/416 |
| 5,700,285 A | | 12/1997 | Myers et al. |
| 5,725,519 A | | 3/1998 | Penner et al. |
| 5,732,530 A | * | 3/1998 | Pfaff ....................... 72/409.19 |
| 5,738,674 A | | 4/1998 | Williams et al. |
| 5,746,764 A | | 5/1998 | Green et al. |
| 5,749,921 A | | 5/1998 | Lenker et al. |
| 5,766,203 A | | 6/1998 | Imran et al. |
| 5,810,871 A | | 9/1998 | Tuckey et al. |
| 5,810,873 A | | 9/1998 | Morales |
| 5,836,952 A | | 11/1998 | Davis et al. |
| 5,836,965 A | | 11/1998 | Jendersee et al. |
| 5,860,966 A | | 1/1999 | Tower |
| 5,893,852 A | | 4/1999 | Morales |
| 5,893,867 A | | 4/1999 | Bagaoisan et al. |
| 5,911,752 A | | 6/1999 | Dustrude et al. |
| 5,992,000 A | | 11/1999 | Humphrey et al. |

FOREIGN PATENT DOCUMENTS

| | | |
|---|---|---|
| DE | 295 06 654.7 | 7/1995 |
| DE | 195 32 288 A1 | 3/1997 |
| EP | 0 630 623 A2 | 12/1994 |
| EP | 0 701 800 A1 | 3/1996 |
| WO | 96/03092 A1 | 2/1996 |
| WO | 97/20593 | 6/1997 |
| WO | 98/19633 | 5/1998 |

* cited by examiner

Primary Examiner—David O. Reip
Assistant Examiner—William Lewis
(74) Attorney, Agent, or Firm—Vidas, Arrett & Steinkraus

(57) ABSTRACT

An apparatus for reducing a medical device such as a stent in size is formed of cooperating crimping dies which are joined via a crimping die moving device. As the cooperating dies are moved together, an inward force is applied to the medical device to reduce the medical device in size.

18 Claims, 9 Drawing Sheets

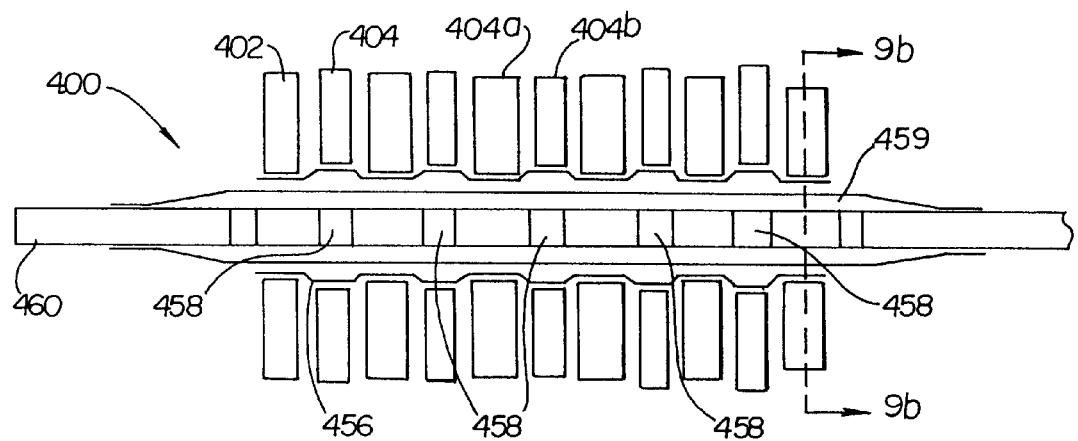
*Fig. 9a*
*Fig. 9b*
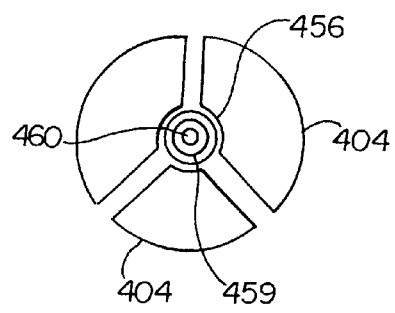
*Fig. 9c*
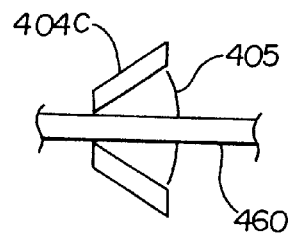
*Fig. 10*
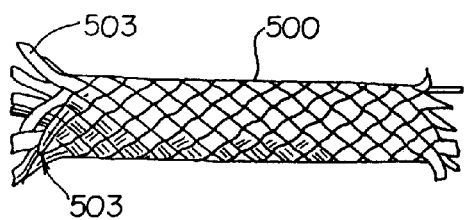

STENT CRIMPING SYSTEM

BACKGROUND OF THE INVENTION

This invention relates to an assembly and a method for fastening a stent onto a catheter. This kind of device finds routine use in the area of percutaneous transluminal coronary angioplasty (PTCA) procedures, although it may be used in other types of procedures, as well.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Inflation expandable stents are well known and widely available in a variety of designs and configurations. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with the crimping of inflation expandable stents although self-expanding stent may be used as well.

An example of an inflation expandable stent is described in PCT Application No. 960 3092 A1, published Feb. 8, 1996, the content of which is incorporated herein by reference.

In advancing an inflation expandable balloon through a body vessel to the deployment site, the stent must be able to securely maintain its axial position on the delivery catheter, without translocating proximally or distally, and especially without becoming separated from the catheter. Stents that are not properly secured or retained to the catheter may slip and either be lost or be deployed in the wrong location or partially deployed. The stent must be crimped in such a way as to minimize or prevent altogether distortion of the stent and to thereby prevent abrasion and/or reduce trauma of the vessel walls. The stent must also be crimped in such a way as to avoid damaging the balloon.

In the past, crimping has been done by hand often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Recently, stent crimping devices have been disclosed in U.S. Pat. No. 5,546,646 to Williams et al, U.S. Pat. No. 5,183,085 to Timmermans et al., U.S. 5,626,604 to Cottone, Jr., U.S. Pat. Nos. 5,725,519, 5,810,873 to Morales, WO 97/20593 and WO 98/19633.

There remains a need to produce a device, optionally portable, to crimp a stent onto a catheter uniformly or reduce a stent in diameter while minimizing the distortion of and scoring and marking of the stent and due to the crimping or size reduction.

In the description that follows it is understood that the invention contemplates crimping a stent either directly to a catheter tube or to a catheter balloon which is disposed about a catheter tube. When reference is made to crimping a stent to a catheter, a balloon may be situated between the stent and the catheter tube or the stent may be crimped to a region of a catheter tube directly.

All U.S. patents and applications and all other published documents mentioned anywhere in this application are incorporated herein by reference in their entirety.

BRIEF SUMMARY OF THE INVENTION

The present invention is directed to an apparatus for reducing a medical device such as a stent in size. The apparatus includes a plurality of jaw-like dies which may be closed inward on the stent to apply an inward directed crimping force to the stent. The dies may be arranged directly opposite one another or may be interleaved. The dies may also be disposed in other configurations as well. A stent may be reduced in size by placing it between the jaw-like dies and moving the dies inward to apply an inward force to the stent. The dies may be moved inward manually or by the use of a suitable actuation device such as an air cylinder or a pneumatic screw.

In one embodiment, the invention is directed to an apparatus for reducing a medical device in size comprising at least one first crimping die with a first crimping surface for contacting the medical device and at least one second crimping die with a second crimping surface for contacting the medical device. The apparatus further comprises a crimping die moving device which connects the first and second crimping dies. The crimping die moving device is constructed and arranged to move the first and second crimping dies toward one another from an open position to a closed position. In the open position, the first and second crimping dies are spaced to form an opening in which a medical device may be inserted. In the closed position, the first and second crimping dies form an opening of reduced size.

In another embodiment, the invention is directed to a stent crimper comprising at least a first crimping die having a first notch therein forming a crimping surface and at least a second crimping die having a projecting portion with a second notch therein forming a crimping surface. The projecting portion is sized to fit at least a part of the way into the first notch in the first crimping die. The crimper further comprises a base portion constructed and arranged to movably receive the first and second dies. The first and second dies are movably received on the base portion with the first and second notches facing each other so as to form a variable size stent receiving region. The first and second crimping dies are movable from an open position in which a stent may be received between the first and second notches to a closed position in which a crimping force is applied to the stent.

In yet another embodiment, the invention is directed to a stent crimper comprising a plurality of linearly arranged, spaced first and second crimping dies. Each first crimping die has a first notch therein forming a crimping surface. Each second crimping die has a second notch therein forming a crimping surface. The crimper further comprises a base portion constructed and arranged to movably receive the first and second crimping dies. The first and second crimping dies are movable from an open position in which a stent may be received between the first and second notches to a closed position in which the first and second crimping dies are interleaved and a crimping force is applied to the stent.

In yet another embodiment, the invention is directed to a stent crimper comprising a plurality of linearly arranged, spaced first crimping dies and linearly arranged, spaced second crimping dies. Each first crimping die has a first notch therein which forms a crimping surface and each second crimping die has a second notch therein which forms a crimping surface. A connecting member connects first and second crimping dies. The first and second crimping dies are movable from an open position in which a stent may be received between the first and second notches to a closed position in which the first and second crimping dies are interleaved and a crimping force is applied to the stent.

In yet another embodiment, the invention is directed to a stent crimper comprising a plurality of linearly arranged die sets which are linearly spaced apart from one another. Each die set comprises a plurality of crimping dies disposed about an open region. Each of the dies in a given die set are disposed radially about a common point, and are movable from an open position in which the open region is sized to receive a stent therethrough to a closed position in which the dies apply a crimping force to the stent. The crimper further comprises at least one actuation device. Each die set is in communication with an actuation device, which may separately control individual dies sets, moving the dies from the open position to the closed position.

In yet another embodiment, the crimper comprises a multiplicity of dies which are disposed at various angles about the longitudinal axis of the stent.

The invention is also directed to a method for reducing a stent or other medical device in size using the inventive apparatus. The medical device is placed in the apparatus in between the first and second crimping dies and the first and second crimping dies moved relatively closer together. An inward force is applied to the medical device thereby reducing the medical device in size. The stent may be placed in a protective sleeve prior to crimping.

The invention also contemplates reducing a stent in size using an inventive crimper as a step in a multistep size reduction and crimping process. A stent may be reduced somewhat in size using any other suitable size reduction technique and then crimped on to a catheter using the inventive apparatus. In one such method, the stent is initially reduced in size by placing it in a braid or other suitable sleeve and elongating the sleeve with a resulting reduction in diameter. The stent is then placed in the inventive apparatus and further reduced in size. Alternatively, the inventive apparatus may be used as a first step in reducing a stent in size prior to crimping the stent onto a catheter.

BRIEF DESCRIPTION OF THE SEVERAL VIEWS OF THE DRAWING(S)

FIG. 1b is a perspective view of a portion of the crimper of FIG. 1a;

FIG. 5b is a perspective view showing the dies used in the inventive stent crimper shown in FIG. 5a;

FIG. 9a shows another embodiment of the invention;

FIG. 9b shows a cross-section of FIG. 9a taken along line 9b—9b;

FIG. 9c shows a cross-section of an angled die; and

FIG. 10 shows a sleeve suitable for enclosing a stent when crimping it in the practice of the invention.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, the term stent refers to stents, stent-grafts, grafts and other endoluminal prostheses whether self-expanding, balloon expandable or a combination of self-expanding and balloon expandable, as are known in the art. Furthermore, where reference is made to crimping a stent, the invention specifically contemplates crimping stents, stent-grafts, grafts and other endoluminal prostheses.

Also, for the purposes of this disclosure, the term 'stent bearing region of a catheter' and similar terms refers to the portion of a catheter about which the stent is to be mounted where no balloon is used to expand the stent and, in the case of balloon expandable stents, refers to the portion of the catheter and balloon about which the stent is to be mounted.

Finally, for the purposes of this disclosure, the term 'crimp' and its cognates shall refer to reducing in size of a stent whether or not the stent is mounted on a catheter. In the later case, the crimping may also result in the stent being conformed, at least in part, to the shape of the catheter or any device mounted between the catheter and the stent.

Figure 1A:
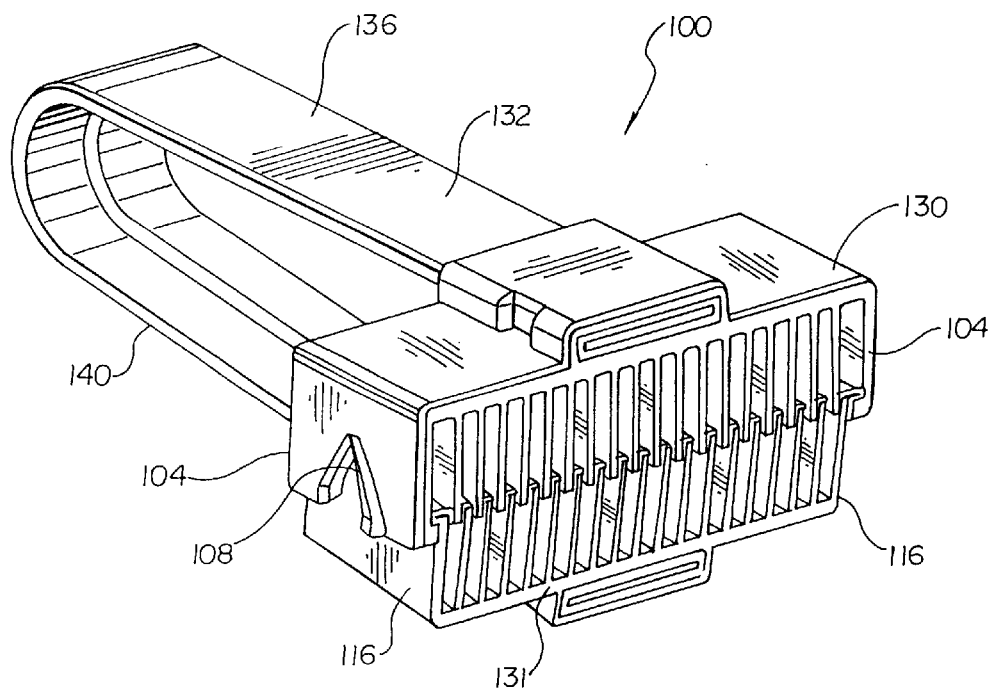
FIG. 1a is a perspective view of an inventive stent crimper.

The present invention is directed generally to an apparatus such as the one shown at 100 in FIG. 1a, for reducing a medical device in size. The apparatus comprises a plurality of first crimping dies 104, a plurality of second crimping dies 116 and a crimping die moving device 132 connecting first crimping dies 104 and second crimping dies 116. First crimping dies 104 are linearly spaced along a first crimping member 130 which is mounted on crimping die moving device 132. Second crimping dies 116 are similarly aligned on a second crimping member 131 which is mounted on crimping die moving device 132.

Figure 2:
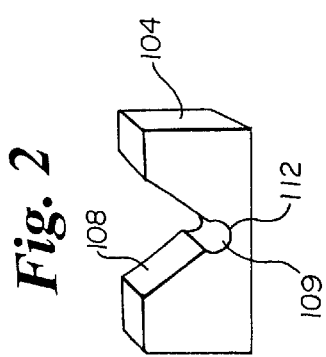
FIG. 2 shows a crimping die.

Each first crimping die 104 and second die 116, as shown in FIG. 1a and 2, has a notch 108 therein forming a crimping surface 109. Notch 108 is substantially V-shaped. The base 112 of the V-shaped notch is desirably arcuate and more desirably, semicircular to accommodate a medical device such as a stent or the like therein. Notches 108 in first crimping dies 104 are aligned so as to be capable of receiving a medical device therein as are notches 108 in second crimping dies 116.

First and second crimping dies 104, 116 are linearly displaced from one another along the length of the crimping members so as to mesh with one another when the crimper is closed. As shown in FIG. 1a, first and second crimping dies 104 and 116 interleave with one another as the crimper is closed.

Figure 1B:
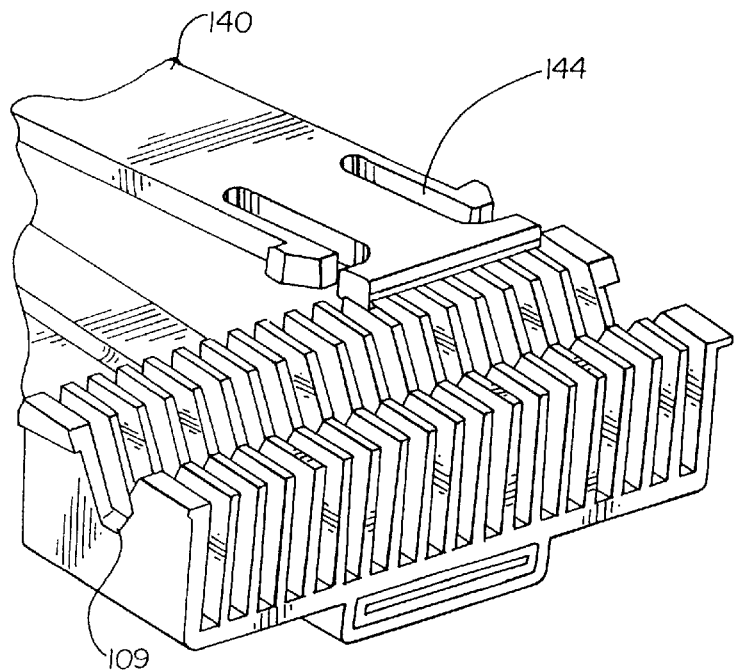

First crimping member 130 and second crimping member 131 extend from crimping die moving device 132. In the embodiment of FIG. 1a, crimping die moving device 132 consists of a first arm 136 and a second arm 140 which are constructed from a single piece of material bent over on itself. Desirably, the first and second arms will have grooves 144 therein, as shown in FIG. 1b, so that first and second crimping dies 104 and 116 may snap into place on first and second arms 136 and 140, respectively. In FIG. 1b, first arm 136 is shown with first crimping dies 104 and first crimping member 130 already in place whereas second arm 140 is shown without second crimping die 116 and second crimping member 131 for the sake of illustrating grooves 144. Other suitable means of mounting the crimping dies and crimping member may be used as well.

The invention also contemplates the first and second arms being formed of separate pieces of material which are then joined together through any suitable technique including bonding, adhesive or otherwise and welding. The two arms are desirably joined at their ends but the junction between the two arms may also be located elsewhere along the arms. Desirably, the crimping die moving device, as shown in FIG. 1a, will be constructed of a resilient metal or plastic such that the apparatus will spring back to its open position where it will remain when released from the closed position.

Figure 3A:
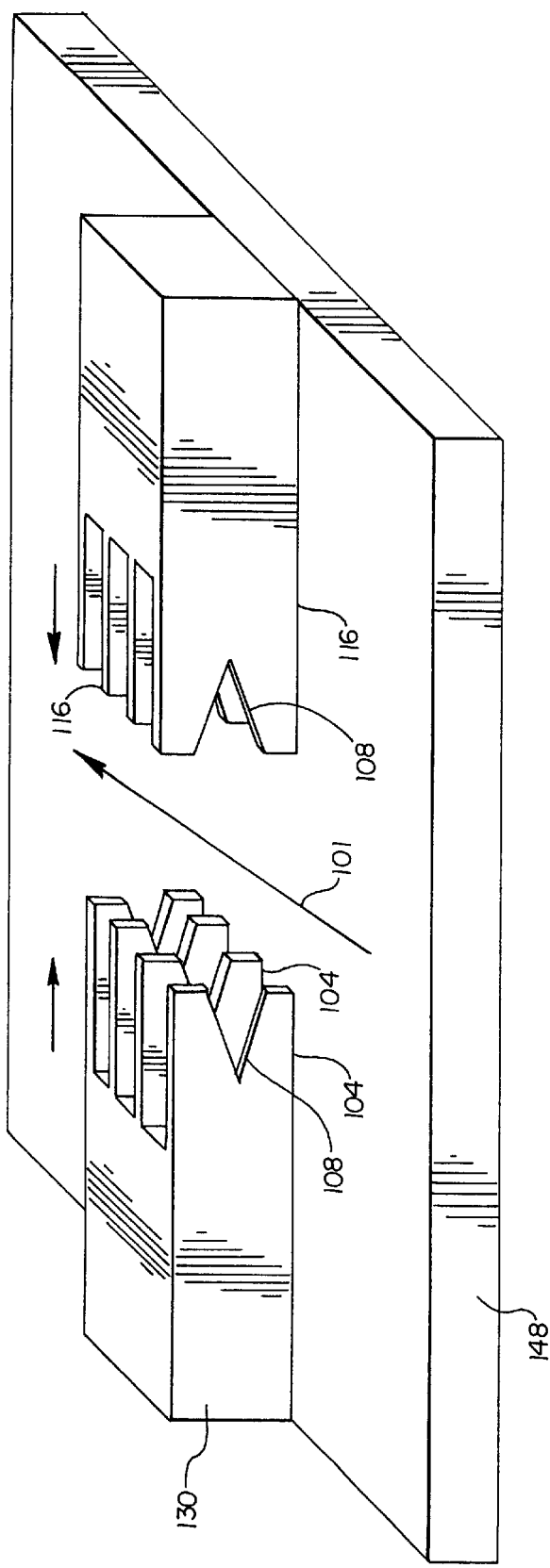
FIG. 3a is a perspective view of an inventive stent crimper in an open position.

In another embodiment of the invention, as shown in FIG. 3a, first crimping dies 104 and second crimping dies 116 are slidingly mounted on a base 148. First crimping dies 104 extend from first crimping member 130 and second crimping dies 116 extend from second crimping member 131. The crimping member and corresponding crimping die may be of single piece or they may be made separately and joined together.

In the embodiment of FIG. 3a, each of the first crimping dies 104 and the second crimping dies 116 have a notch therein. Desirably, although not shown in FIG. 4a, notch 116 will have an arcuate or semicircular portion similar to that shown in FIG. 2.

First crimping dies 104 and second crimping dies 116 are longitudinally displaced from one another so that the dies will mesh when as the crimper is closed, as shown in FIG. 4b.

Figure 3B:
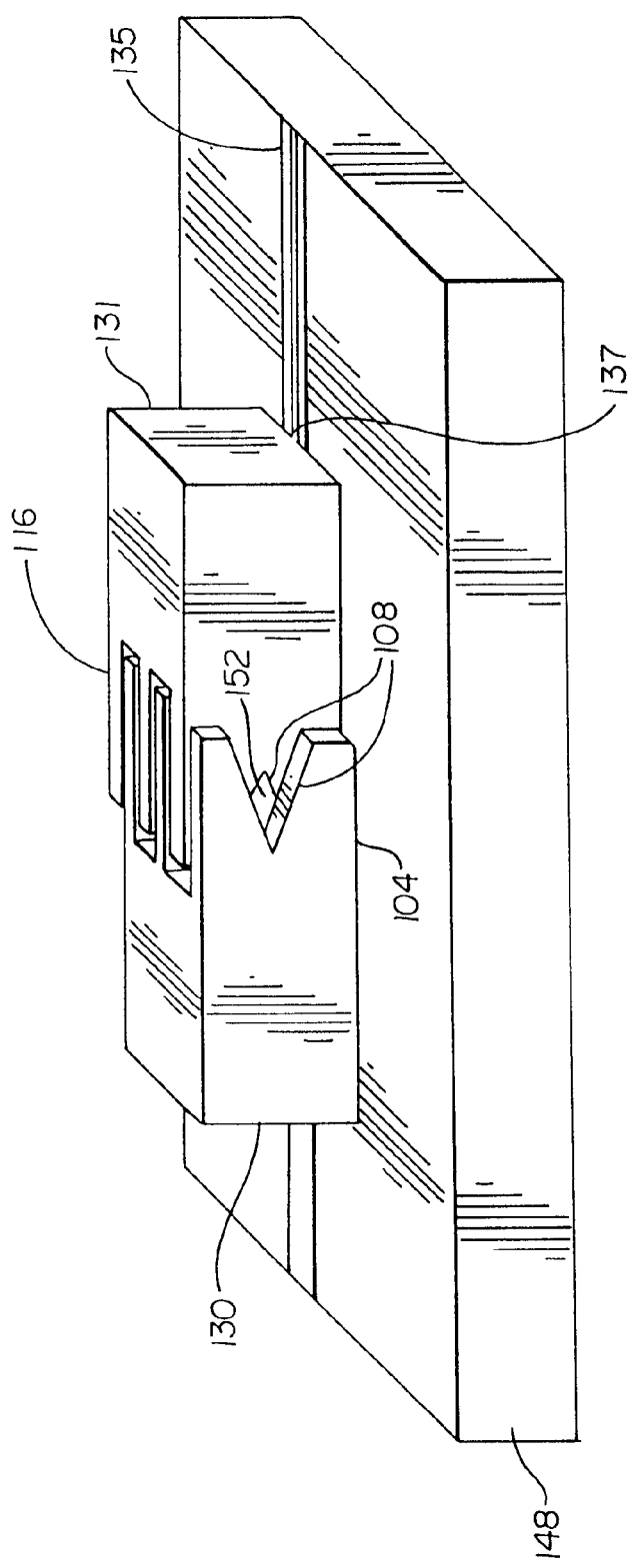
FIG. 3b is a perspective view of the inventive stent crimper of FIG. 3a in a closed position.
Figure 3C:
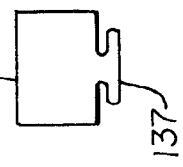
FIG. 3c is side elevational view of a crimping die.

As further shown in FIGS. 3b and 3c, base 148 has a groove 135 cut therein which slidingly receives rail 137 which extends from each of first crimping die moving member 130 and second crimping device moving member 131. Those of ordinary skill in the art will recognize other suitable ways for slidingly mounting the moving members to the base.

In use, a stent or other suitable medical device is inserted in the space between the first and second crimping dies and the dies slid together to reduce the diameter of the stent or other suitable device. When the crimper is closed, the opening between the first dies 104 and the second dies 116, designated by reference numeral 152, is reduced in size, as illustrated in FIG. 3b. In normal use, a stent or other medical device, whether by itself or disposed about a catheter will rest in opening 152.

In a related embodiment, an apparatus similar to that shown in FIG. 3a may be constructed in which only one of the sets of crimping dies is slidable. In use, a stent is disposed between the crimping dies and the slidable crimping dies slid toward the fixed crimping dies to reduce the diameter of the stent.

The crimper of FIGS. 1 and 3 is a self-centering crimper. Stents inserted between the notches in the first and second dies will self-center in the notches upon closure of the dies.

Figure 4:
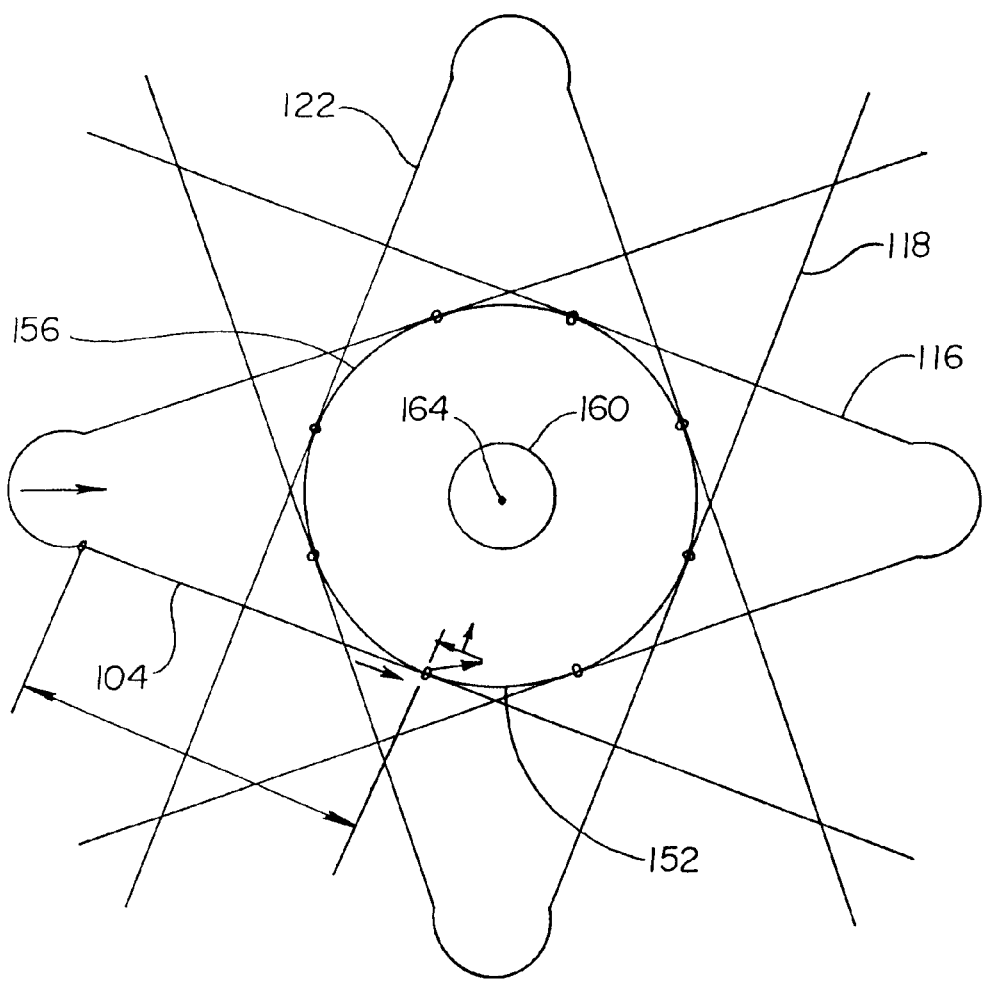
FIG. 4 is a schematic of an inventive stent crimper comprising two sets of opposing crimping dies.

The invention also contemplates embodiments having additional crimping dies arranged at various angles about the longitudinal axis of the crimper. FIG. 4 is a schematic drawing of an embodiment in which four sets of crimping dies are provided. First and second crimping dies 114 and 116 are disposed opposite one another and longitudinally displaced from one another as are third and fourth crimping dies 118 and 122, moreover, third and fourth crimping dies 118 and 122 are rotated 90° with it to the first and second crimping dies. Stent 156 is shown disposed about catheter 160 in opening 152. Additional sets of crimping dies disposed at other angles may also be provided. Desirably, the sets of crimping dies will be arranged such that in the closed position they are regularly disposed about the opening between them. As shown in FIG. 4, the crimping dies are regularly disposed abut a common point 164. Depending on the form of the dies, the dies may be interleaved or directly opposite one another.

In use, the sets of opposing dies may be applied simultaneously or sequentially. In the latter case, the third and fourth die sets may be closed and released after the first and second die sets have been utilized and removed thereby ensuring that each die set is able to contact and crimp the stent as desired regardless of the spacing of the dies.

The invention contemplates embodiments having an even number of sets of crimping dies as well as embodiments having an odd number of crimping dies. In the latter case, none of the sets of crimping dies need be opposite one another.

Figure 5A:
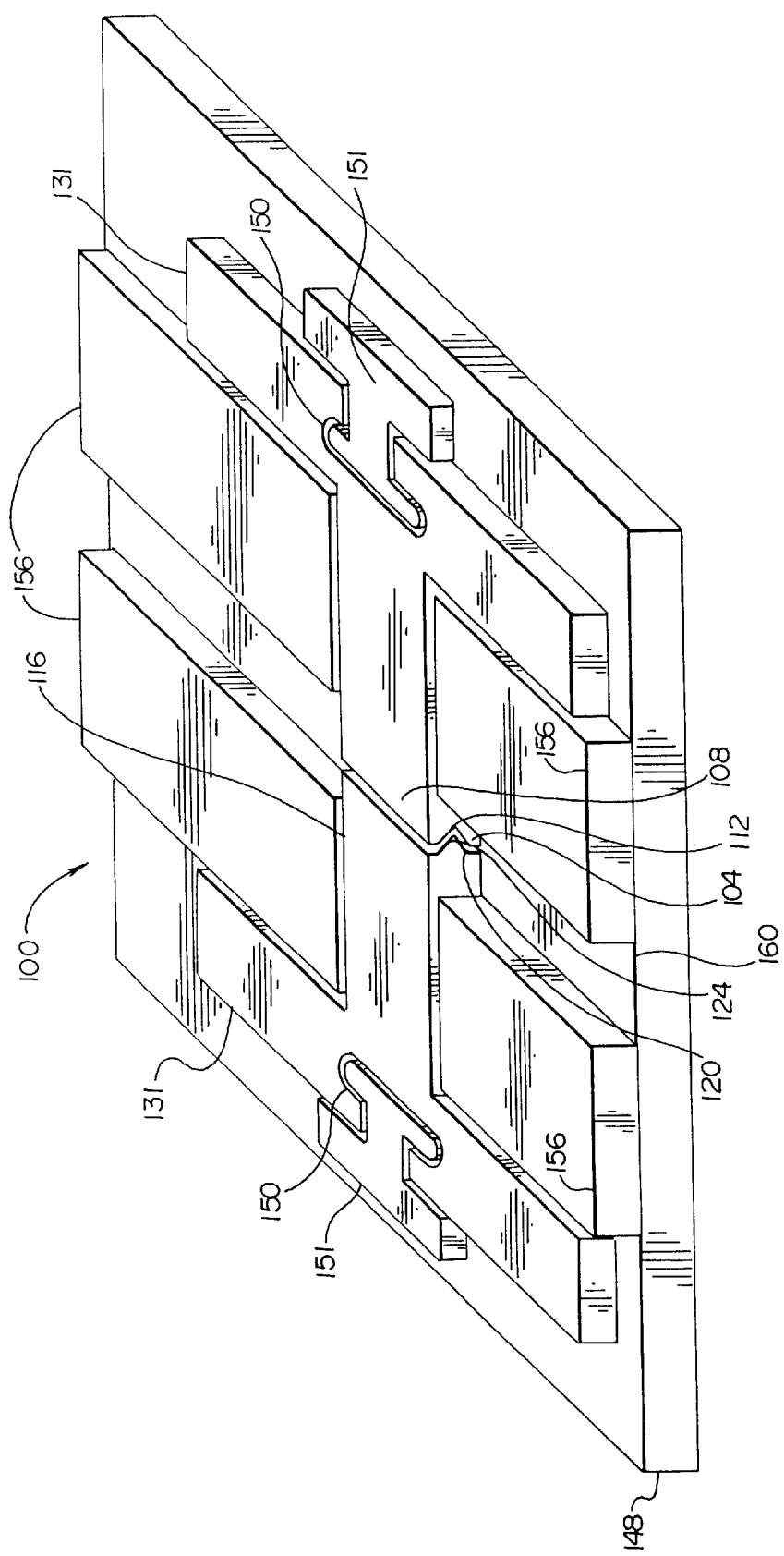
FIG. 5a is a perspective view of an inventive stent crimper.
Figure 5B:
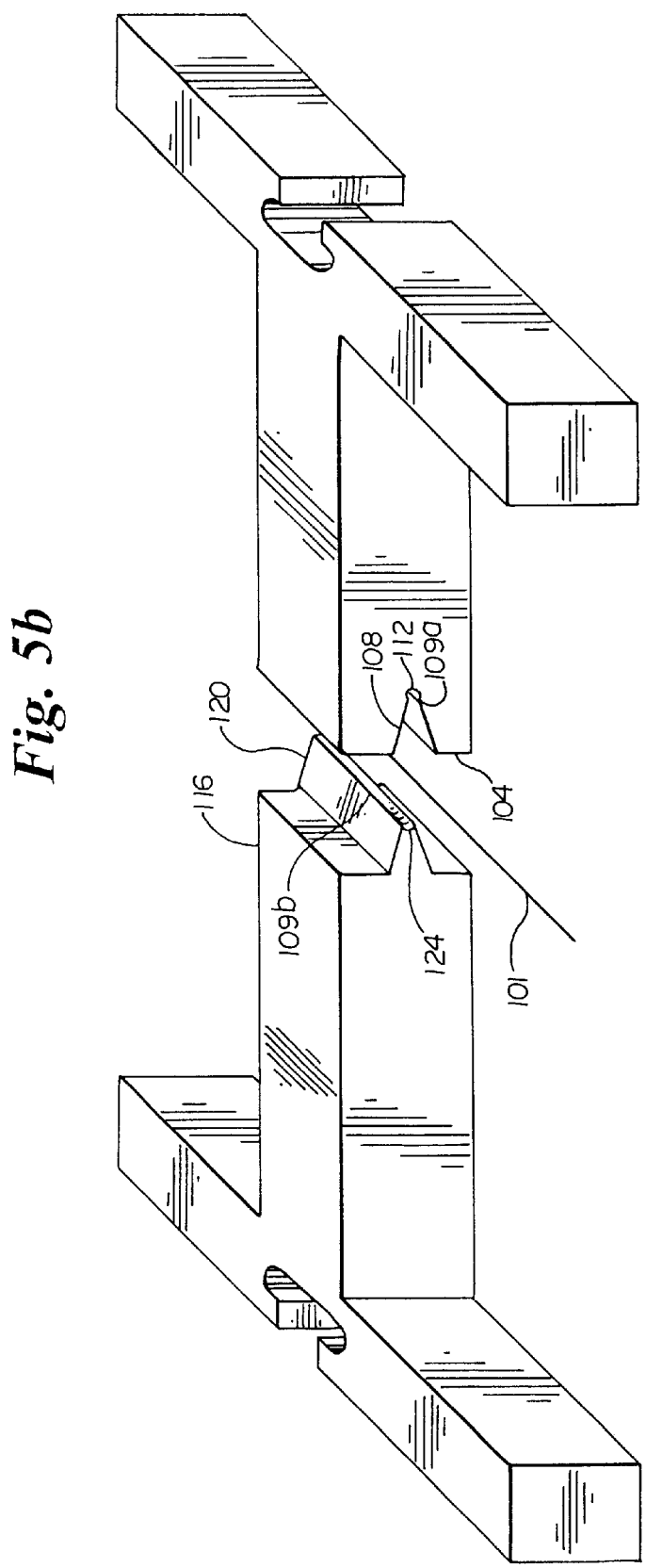

In yet another embodiment, the inventive apparatus comprises a single first crimping die 104 and a single second crimping die 116 as shown generally at 100 in FIGS. 5a and 5b. Desirably, first and second crimping dies 104 and 116 will be at least as long as the stent or other medical device to be crimped. First and second crimping dies 104 and 116 extend from first and second crimping members 130 and 131 respectively. First and second crimping dies 104 and 116, respectively, are longitudinally aligned in that the dies are not linearly displaced along the longitudinal axis 101 of the crimping device.

First crimping member 130 and second crimping member 131 each include an optional opening therein 150 to receive a device, such as an air cylinder or a pneumatic screw, shown schematically at 151 in FIG. 5a, which is capable of moving the crimping members inward and outward. The dies may also be hand operated.

As shown in FIG. 5a, first and second dies 104 and 116 rest upon base 148. Base 148 includes four raised portions 156 which form a cradle for first and second dies 104 and 116. Raised portions 156 also include a channel 160 in which a catheter may reside.

It is noted that the dies such as those shown in FIGS. 5a and 5b in any of the other crimping apparatuses shown in this disclosure.

Figure 6:
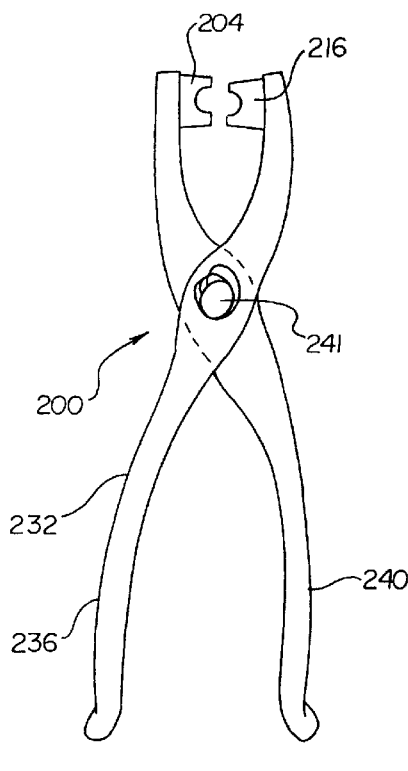
FIG. 6 is a front view of another embodiment of the invention.

In yet another embodiment, shown generally at 200 in FIG. 6 the inventive crimper includes a first crimping die 204, a second crimping die 216 and a crimping die moving device 232 connecting first crimping die 204 and second crimping die 216. Crimping die moving device 232 includes first arm 236 and second arm 240 which are pivotally interconnected by fastener 241.

First and second crimping dies 204 and 216 each have an arcuate or semicircular notch 208 therein. Notch 208 is sized to hold a stent therein.

Crimping dies 204 and 216 may be adhesively bonded or otherwise attached to arms 236 and 240 or formed integrally with the arms. The crimping members may also be removably attached to arms 236 and 240 for ease of changing members based on the specific crimping needs.

In use, a stent or other suitable medical device is inserted between first crimping die 204 and second crimping die 216 and first arm 236 and second arm 240 are moved relatively closer together. An inward force is thus applied to the stent or other medical device. The arms may then be moved apart to facilitate removal of the stent.

The present application is also directed to stent crimpers capable of non-uniformly crimping a stent on a catheter and methods of non-uniformly crimping a stent to a catheter.

Additional crimping of the end portions provides for an increased stent securement force relative to a crimped stent with a continuous inner and outer diameter profile. The additional crimping also provides atraumatic proximal and distal stent edges for advancement and withdrawal of the stent through delivery guides and vasculature thus reducing the likelihood that the stent will snag on the interior of a vessel or delivery guide. Any of the devices described above can be modified simply in order to apply the additional crimping force to the stent in the desired regions of the stent.

Figure 7A:
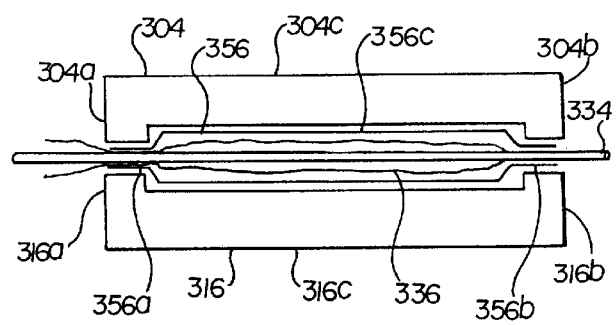
FIG. 7a is a side view of a crimping die for preventing stent flaring.

A suitable crimping die for crimping the proximal and distal ends of a stent relative to the remainder of the stent to avoid flaring of the stent ends upon expansion of the stent is shown at 304 and 316 in FIG. 7a. First ends 304a, and 316a respectively and second ends 304b and 316b, respectively, extend further inward than intermediate portions 304c and 316c, respectively. As dies 304 and 316 come together, ends 356a and 356b of stent 356 are reduced to a smaller diameter than intermediate portion 356c.

Dies 304 and 316 may be used in conjunction with the crimping die moving device 232 shown in FIG. 6 or other suitable crimping die moving devices disclosed herein. A non-uniform crimp may also be realized using devices such as those shown in FIGS. 1, 3a, b, and 4 by providing an array of first crimping dies and an array of second crimping dies, each array including at least one crimping die at each end which, when taken along with the opposing die, defines a smaller diameter opening.

Figure 8:
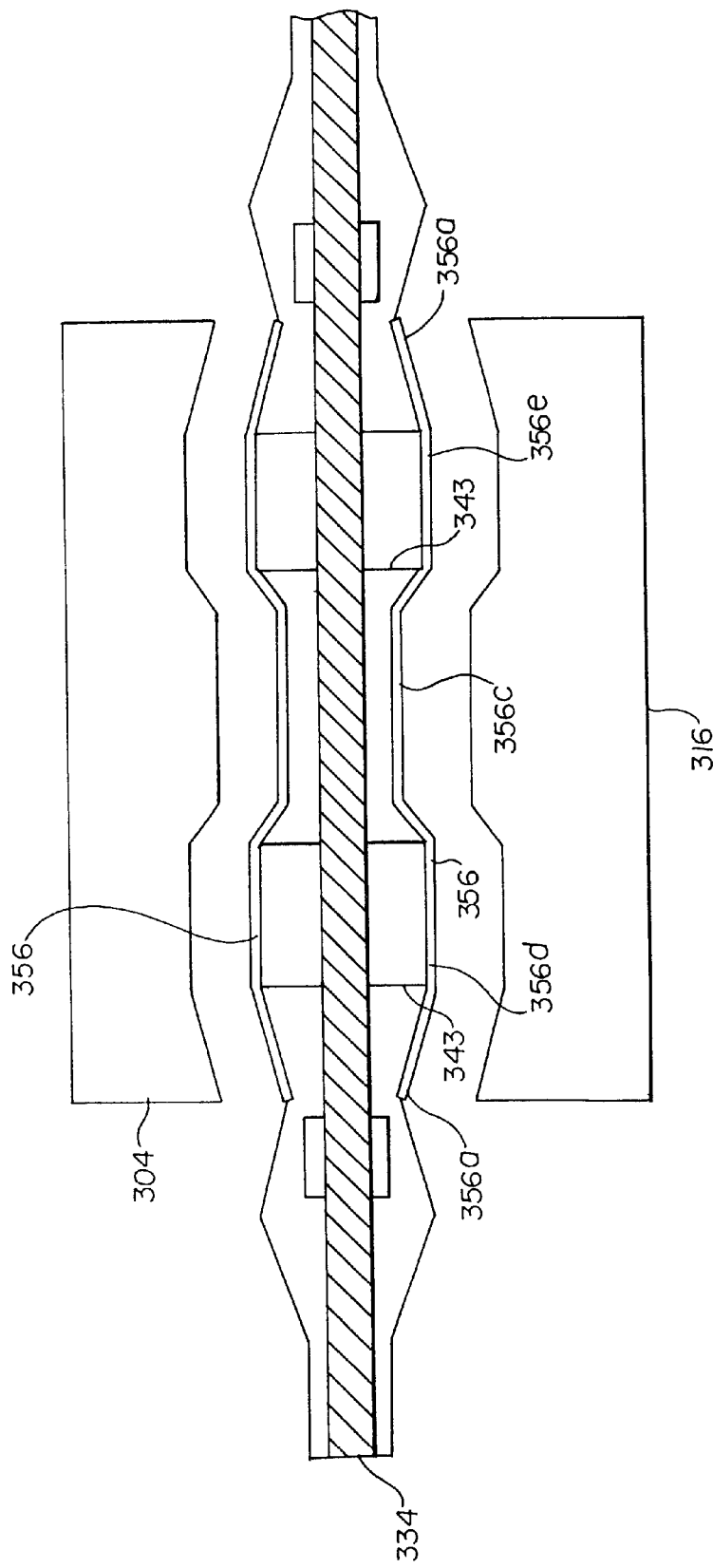
FIG. 8 is a side view of a crimping die for achieving a non-uniform crimping of a stent.

Non-uniform dies may also be useful in crimping a stent to a catheter which has suitable mounting devices extending therefrom. As shown in FIG. 8, catheter 334 has two stent support bands 343 mounted thereon. Stent 356 has been crimped using dies 304 and 316. The shape of dies 304 and 316 conforms to the profile of catheter 334 and stent support bands 343. Stent 356, having been crimped by dies 304 and 316, conforms to the catheter and support bands.

Figure 7B:
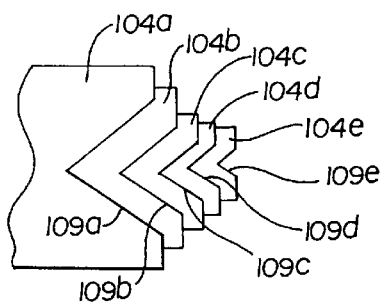
FIG. 7b is a perspective view of an arrangement of crimping dies.
Figure 7C:
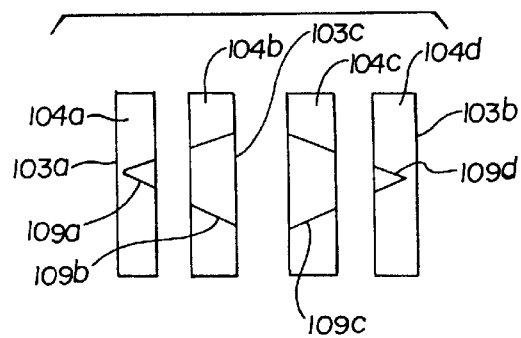
FIG. 7c is a front view of an arrangement of crimping dies.
Figure 7D:
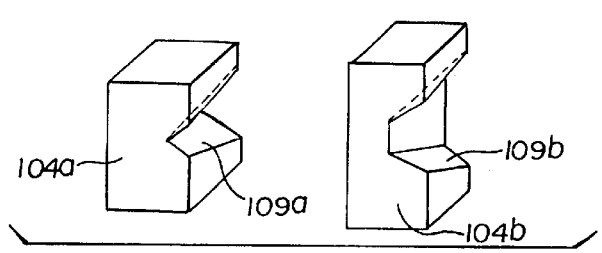
FIG. 7d is a perspective view of an arrangement of crimping dies.

The embodiment of FIG. 7a may also be realized by mounting dies 304 and 316 in a manner similar to that shown in FIG. 5a. The inventive concept may also be realized by providing a plurality of first and second crimping dies as in FIGS. 1, 3a, 3b and 4 which define suitable openings therebetween along the length of the stent. FIG. 7b shows an arrangement of individual crimping dies 104a–e, each having a crimping surface 109a–e in the form of a V-shaped notch. The V-shaped notch grows progressively smaller from die 104a to die 104e. FIG. 7c shows a front view of an arrangement of dies 104a–d with notches 109a–d that grow progressively deeper from sides 103a,b of the arrangement to center 103c of the arrangement. FIG. 7d shows a perspective view of two of the dies of FIG. 7c. It is, of course, understood that two such sets of opposing, interleaved dies are necessary to form the inventive stent crimper.

In another embodiment of the invention, movement of the dies may be controlled by actuators which are arranged so as to output a desired force. The force applied to the various die may differ depending on the location of the die.

As shown in FIG. 9a, the stent crimper, shown generally at 400, comprises at least one die set, shown generally at 402 and desirably a plurality of side-by-side dies sets which define an opening for receiving a stent therein. Die sets 402 includes a plurality of individual dies 404. As shown in FIG. 9b, each die 404 has an annular inner surface 405. The invention may also be practiced using die sets which comprise two dies or die sets which comprise four or more individual dies. Dies 404 in a given die set 402 form an annulus when they are completely closed.

Each die set is individually controlled by an actuation device which controls how much force is applied to the dies in a given die set. As soon as a desired force is achieved, the die is held in position until the desired force is achieved for the remaining dies, at which point the dies are released. The actuation device may include air cylinders or pneumatic screws and a suitable control system. Other commercially available actuation systems may be used as well. Desirably, the actuators will be set so that each of the individual dies applies equal pressure to the stent The invention further contemplates the use of dies of differing lengths depending on the region of the stent to be crimped. In FIG. 9a, for example, first dies 404a are longer than second dies 404b. The length of second dies 404b corresponds to the length of stent securement hubs 458 on catheter 460 underneath stent 456. Stent 456, shown in FIG. 9a, has already been crimped in accordance with the invention to balloon 459 and catheter 460.

The inventive stent crimper may further comprise angled dies at the ends, such as die 404c, shown in cross section in FIG. 9c, to reduce flaring of the stent ends.

The invention is further directed to methods of crimping a stent or other medical device using the inventive apparatuses disclosed herein.

In one embodiment, a stent or other medical device is disposed between the crimping dies of the apparatuses disclosed herein. The first and second crimping dies are then moved relatively closer together such that an inward force is applied to the medical device thereby reducing the medical device in size. The method may be used to crimp a stent uniformly or non-uniformly. An example of the latter is shown in FIG. 8. Stent 356 is crimped to a non-uniform diameter along its length. Ends 356a,b are tapered. Middle portion 356c and intermediate portions 356d,e are crimped to different diameters (or, in the case of a stent with a substantially non-circular transverse cross-section, to different transverse cross-sectional areas).

The stent or medical device may simply be reduced in size via the inventive method or may be crimped onto a catheter using the inventive method.

In another embodiment, a first crimping force is applied to some of the crimping dies in the above inventive apparatuses and a second and different crimping force is applied to some other of the dies to facilitate crimping. The application of different forces to different dies is particularly useful in crimping a stent to a catheter having stent securement hubs or other non-uniformities in the catheter surface.

In all of the above embodiments, the stent may further be protected by a sleeve to prevent direct contact between the stent and the crimping device. This may minimize or eliminate any marring or nicking of the stent by the crimping member. Suitably the sleeve is comprised of elastomeric tubing, although more generally, polymeric tubing may be used. The sleeve may also be formed of a braided material. In particular, a sleeve which has a full diameter and at least one reduced diameter configuration when a tension is applied to the sleeve may be used to protect the stent and to supply an additional crimping force to the stent.

A preferred embodiment of a protective sleeve formed of braided material is indicated at 500 in FIG. 10. In the embodiment shown polymeric or metal braids may be used. Individual strands 503 of a given polymer are interwoven as shown in FIG. 10 to form tubular braid 500. Moreover, the weave must be dense enough as to prevent parts of the stent, depending on the design of the stent, from penetrating the weave and becoming enmeshed in it. In a preferred embodiment, individual strands 503 are made of Nylon having a circular cross section of diameter 5/1000 inch. Strands 503 are woven together in a clothing weave to form tubular braid 500 with the weave being about 20 to about 90 picks/inch, desirably about 55 picks/inch. An example of a braid tube braid tube is one manufactured by SCIMED Life Systems, Inc., Maple Grove, Minn. and/or SantaFe Textiles, Inc., Los Angeles, Calif. Suitable ones may be manufactured by any other coil braider. Nylon or polypropylene propylene may also be used for the braid as well as other suitable polymeric materials including elastomeric materials. The sleeve may also be provided in the form of a smooth polymeric tube.

In addition to protecting the stent, the protective sleeve may also be used to reduce the stent in size prior to the stent being crimped. By stretching the sleeve a radially inward may be applied to the stent.

A typical crimping sequence that includes the use of the protective sleeve includes the following steps:

1) presize stent using any suitable means (optional);
2) load stent onto balloon and catheter (optional);
3) place sleeve (optionally longer than the stent) over stent (optional);
4) position stent between opposing dies of an inventive stent crimper;
5) crimp the stent;
6) rotate the stent by a desired amount, such as 9° (optional);
7) slide sheath forward on stent to bring stent into contact with a portion of the sleeve that has not been crimped (optional);
8) crimp the stent (optional);
9) rotate stent again by a desired amount, desirably 45° in a direction opposite to the prior direction of rotation (optional);
10) slide sheath forward on stent to bring stent into contact with a portion of the sleeve that has not been crimped (optional); and
11) crimp the stent (optional).

The rotating, sliding and crimping steps may be repeated, as necessary, until a desired final configuration is reached.

Additional crimping steps may be applied to the stent following the above sequence.

The invention is further directed to methods of crimping in which any of the individual crimping modalities disclosed herein is combined in sequence with any other crimping modality disclosed herein and/or with any of the crimping modalities described in the commonly assigned, cofiled U.S. patent application Ser. Nos. 09/401,467, 09/404,986, and 09/401,218, and commonly assigned and copending U.S. application Ser. No. 08/951,550 all of which are directed to stent crimpers and all of which are incorporated herein in their entirety by reference. Thus, a stent may be pre-crimped using one crimping technique and further crimped using another crimping technique.

The above disclosure is intended to be illustrative and not exhaustive. This description will suggest many variations and alternatives to one of ordinary skill in this art. All these alternatives and variations are intended to be included within the scope of the attached claims.

In addition to being directed to the specific combinations of features claimed below, all possible alternative dependent combinations of the features recited above or in the dependent claims, whether written in multiple dependent form or not, should be considered to be within the scope of the invention. Those familiar with the art may recognize other equivalents to the specific embodiments described herein which equivalents are also intended to be encompassed by the claims attached hereto.

We claim:

1. An apparatus for reducing a medical device in size comprising:
    at least one first crimping die with a first crimping surface for contacting the medical device;
    at least one second crimping die with a second crimping surface for contacting the medical device; and
    a crimping die moving device which connects the first and second crimping dies,
        the crimping die moving device comprising a base from which the first and second crimping dies extend,
        at least one of the crimping dies slidably mounted in the base,
        the crimping die moving device constructed and arranged to move the first and second crimping dies toward one another from an open position to a closed position,
        the first and second crimping dies in the open position spaced to form an opening in which a medical device may be inserted,
        the first and second crimping dies in the closed position forming an opening of reduced size.

2. The apparatus of claim 1 wherein both the first and second crimping dies are slidably mounted in the base.

3. An apparatus for reducing a medical device in size comprising:
    at least one first crimping die with a first crimping surface for contacting the medical device;
    at least one second crimping die with a second crimping surface for contacting the medical device; and
    a crimping die moving device which connects the first and second crimping dies, the crimping die moving device comprising at least one air cylinder, the at least one air cylinder in mechanical communication with at least one of the first and second crimping dies,
        the crimping die moving device constructed and arranged to move the first and second crimping dies toward one another from an open position to a closed position,
        the first and second crimping dies in the open position spaced to form an opening in which a medical device may be inserted,
        the first and second crimping dies in the closed position forming an opening of reduced size.

4. An apparatus for reducing a medical device in size comprising:

a plurality of first crimping dies, each of the plurality of first crimping dies having a first crimping surface for contacting the medical device, the first crimping surface of one or more of the plurality of first crimping dies differing in shape from the crimping surface of the remaining first dies;

a plurality of second crimping dies, each of the plurality of second crimping dies having a second crimping surface for contacting the medical device, the second crimping surface of one or more of the plurality of second crimping dies differing in shape from the crimping surface of the remaining second dies; and a crimping die moving device which connects the plurality of first crimping dies and the plurality of second crimping dies, the crimping die moving device constructed and arranged to move the plurality of first crimping dies and the plurality of second crimping dies toward one another from an open position to a closed position, the plurality of first crimping dies and the plurality of second crimping dies in the open position spaced to form an opening in which a medical device may be inserted, the plurality of first crimping dies and the plurality of second crimping dies in the closed position forming an opening of reduced size.

5. An apparatus for reducing a medical device in size comprising:

a plurality of first crimping dies, each of the plurality of first crimping dies having a first crimping surface for contacting the medical device;

a plurality of second crimping dies, each of the plurality of second crimping dies having a second crimping surface for contacting the medical device; and a crimping die moving device which connects the plurality of first crimping dies and the plurality of second crimping dies, the crimping die moving device constructed and arranged to move the plurality of first crimping dies and the plurality of second crimping dies toward one another from an open position to a closed position, the plurality of first crimping dies and the plurality of second crimping dies in the open position spaced to form an opening in which a medical device may be inserted, the plurality of first crimping dies and the plurality of second crimping dies in the closed position forming an opening of reduced size, the crimping die moving device further constructed and arranged to apply a first force to one or more of the plurality of first crimping dies and one or more second dies and a second force to one or more other first crimping dies and one or more other second crimping dies.

6. The apparatus of claim 5 wherein the first and second crimping dies are longitudinally aligned.

7. The apparatus of claim 5 comprising a plurality of third crimping dies in mechanical communication with the crimping die moving device, the first, second and third crimping dies longitudinally aligned.

8. The apparatus of claim 5 wherein the second force is different from the first force.

9. A method of crimping a stent comprising the steps of:
a) loading the stent onto a balloon and catheter;
b) providing a stent crimper, the stent crimper comprising:
at least one first crimping die with a first crimping surface for contacting the stent;
at least one second crimping die with a second crimping surface for contacting the stent; and
a crimping die moving device which connects the first and second crimping dies, the crimping die moving device constructed and arranged to move the first and second crimping dies toward one another from an open position to a closed position,
the first and second crimping dies in the open position spaced to form an opening in which a medical device may be inserted,
the first and second crimping dies in the closed position forming an opening of reduced size;
c) positioning the stent between the first crimping die and the second crimping die of the stent crimper
d) applying a crimping force to the stent;
e) rotating the stent by a predetermined angle about its longitudinal axis;
f) applying a crimping force to the stent.

10. The method of claim 9 wherein a sheath is disposed about the stent prior to applying a crimping force to the stent.

11. The method of claim 10 wherein the sheath is longer than the stent and the sheath is moved relative to the stent in between applying steps.

12. The method of claim 9 wherein the stent is rotated by about 90° during step e).

13. The method of claim 9 further comprising the steps of:
g) rotating the stent by a predetermined angle about its longitudinal axis; and
h) applying a crimping force to the stent, p1 steps g) and h) occurring subsequent to step f).

14. The method of claim 13 wherein the stent is rotated by about 90° during step e) and by about 45° during step g).

15. The method of claim 9 where a non-uniform crimping force is applied to the stent during at least one of steps d) and f).

16. The method of claim 9 wherein the stent is crimped to a nonuniform diameter.

17. A method of crimping a stent comprising the steps of:
providing a stent disposed about a region of a catheter, the region having a non-uniform transverse cross-section;
applying a non-uniform crimping force to the stent.

18. The method of claim 17 wherein the applying step comprises the steps of:
applying a first crimping force to a first portion of the stent; and
applying a second crimping force to a second portion of the stent, the first force different from the second force.

* * * * *